(12) United States Patent
Sabatini et al.

(10) Patent No.: US 10,246,428 B2
(45) Date of Patent: Apr. 2, 2019

(54) INSENSITIVE PLASTICIZER AND MELT-CASTABLE ENERGETIC MATERIAL

(71) Applicant: THE UNITED STATES OF AMERICA AS REPRESENTED BY THE SECRETARY OF THE ARMY-U.S. ARMY RESEARCH LABORATOR, Washington, DC (US)

(72) Inventors: Jesse J. Sabatini, Bel Air, MD (US); Gregory W. Drake, Madison, AL (US); Leah A. Wingard, Landenberg, PA (US); Eric C. Johnson, Millington, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 15/686,195

(22) Filed: Aug. 25, 2017

(65) Prior Publication Data

US 2019/0062287 A1 Feb. 28, 2019

(51) Int. Cl.
*C07D 261/08* (2006.01)
*C06B 25/00* (2006.01)

(52) U.S. Cl.
CPC ............ *C07D 261/08* (2013.01); *C06B 25/00* (2013.01)

(58) Field of Classification Search
CPC .................................................. C07D 261/08
USPC ....................................................... 548/247
See application file for complete search history.

(56) References Cited

U.S. PATENT DOCUMENTS 9,296,664 B2    3/2016    Klapotke et al.

OTHER PUBLICATIONS

Wingard, L., P. Guzman, E. Johnson, J. Sabatini, G. Drake and E. Byrd, "Synthesis of bis-Isoxazole-bis-Methylene Dinitrate: A Potential Nitrate Plasticizer and Melt-Castable Energetic Material", ChemPlusChem (2017), 82: pp. 195-198. (Year: 2016).*
Sausa, S., R. Pesce-Rodriguez, L. Wingard, P. Guzman and J. Sabatini, "Crystal structure of 3,3'-biisoxazole-5,5'-bis-(methylene) dinitrate (BIDN)" Acta. Cryst. (2017), E73: pp. 644-646. (Year: 2017).*
Wingard, L., E. Johnson, P. Guzman, J. Sabatini, G. Drake, E. Byrd and R. Sausa, "Synthesis of Biisoxazoletetrakis(methyl nitrate): A Potential Nitrate Plasticizer and Highly Explosive Material" Eur. J. Org. Chem., (2017), pp. 1765-1768. (Year: 2017).*
Van der Peet, Philip, et al. "A click chemistry approach to 5,5'-Disubstituted-3,3'-Bisisoxazoles from dichloroglyoxime and alkynes: Luminescent organomettalic Iridium and Rhedium Bisisoxazole complexes" Journ. Org. Chem. (2013), 78: pp. 7298-7304. (Year: 2013).*

* cited by examiner

*Primary Examiner* — Matthew P Coughlin
*Assistant Examiner* — Sagar Patel
(74) *Attorney, Agent, or Firm* — Robert Thompson; Eric Brett Compton

(57) ABSTRACT

A method and compound includes mixing dichloroglyoxime with an alcohol containing an alkyne functional group in methanol to create a mixture; adding a salt compound and water to the mixture to create bis-isoxazole diol; and nitrating the bis-isoxazole diol to create 3,3'-bis-isoxazole-5,5'-bis-methylene dinitrate, which has the structural formula:

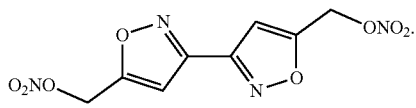

The alcohol containing an alkyne functional group may include propargyl alcohol. The salt compound may include sodium bicarbonate. The method may include nitrating the bis-isoxazole diol with nitric acid. The nitric acid may include at least a concentration of 90% nitric acid in water. Alternatively, the method may include nitrating the bis-isoxazole diol with 100% nitric acid and acetic anhydride. The salt compound and the water may be added to the mixture over at least a six-hour period. The method may include mixing the mixture after adding the salt compound and the water for at least ten hours.

20 Claims, 11 Drawing Sheets

INSENSITIVE PLASTICIZER AND MELT-CASTABLE ENERGETIC MATERIAL

GOVERNMENT INTEREST

The embodiments herein may be manufactured, used, and/or licensed by or for the United States Government without the payment of royalties thereon.

BACKGROUND

Technical Field

The embodiments herein generally relate to energetic materials, and more particularly to energetic materials used in explosives and propellants.

Description of the Related Art

The development of high-energy density materials (HEDMs) with good performance and low sensitivity is a common goal amongst those with an interest in the field of energetic materials. HEDMs are divided into two main groups: explosives and propellants. Explosive materials contain a significant amount of potential energy that produces a significant amount of light, heat, sound and pressure when this energy is released suddenly. When this phenomenon occurs, it is known as an explosion. A propellant is an energetic substance that is used to project a vehicle, bullet or other object, typically through the formation of hot, low molecular weight gases.

Two respective sub-areas of explosives and propellants are melt-castable materials and energetic plasticizers. It is known in the industry that an ideal melt-cast material is defined as having a low vapor pressure (inhalation toxicity), a melting point between 70-120° C., a significant difference between the melting temperature and the temperature of decomposition, a high density, low sensitivity, and a "greener" synthesis. Traditional melt-cast technologies are TNT-based, but environmental concerns have led to its replacement with dinitroanisole (DNAN)-based melt-castable eutectic formulations, as known in the industry. However, DNAN, with a density of 1.52 gcm$^{-3}$, and a detonation velocity of 5670 ms$^{-1}$, is a less powerful explosive than TNT according to conventional thought. Thus, there is an interest in developing new melt-castable candidates that can be formulated to probe their potential applications.

As the name implies, a plasticizer, when added to a formulation, enhances the fluidity or plasticity of the material. Energetic plasticizers are used to improve the physical properties, to double as a fuel, and to improve the overall energy yield of a formulation. Currently, most fielded nitrate-based plasticizers are high-energy molecules, which to the formulator, are as oxygen balanced as possible to obtain the highest performance of their respective propellant (gun and rocket). One of the most popular nitrate ester-based plasticizers is the oily liquid nitroglycerin (NG). Moreover, a very useful and applicable gel is formed when NG is mixed with nitrocellulose (NC). This gel has been used for many years to produce blasting gelatin, gelatin dynamite, and ballistite, the first double-base propellant smokeless powder. NC and NG make up an optimal energetic composition. The former helps impart mechanical strength to the propellant, while the latter assists in increasing the energy and burning rate of the propellant.

Unfortunately, oxygen balanced nitrate-based plasticizers such as NG tend to be quite sensitive to a variety of thermal and mechanical insults. Typically, most liquid nitrates have rather high volatility in regards to their molecular weight. Coupled with weak carbon-nitroxy linkages, it has been shown that this often results in premature volatilization/decomposition into reactive gaseous products under extended heating/and or long-term aging, resulting in detonable materials. Unfortunately, NG, which widely regarded as the work horse energetic plasticizer, suffers from a high degree of thermal instability, as it decomposes at 50° C. NG also tends to require chemical stabilization, as it is so reactive to be used in practical applications as a standalone ingredient. Hence, energetic plasticizers such as NG suffer from high volatility in cook-off scenarios, leading to gas phase species which are highly detonable. Accordingly, there is a need to develop new energetic materials that overcome the aforementioned safety concerns.

SUMMARY

In view of the foregoing, an embodiment herein provides a method comprising mixing dichloroglyoxime with an alcohol containing an alkyne functional group in methanol to create a mixture; adding a salt compound and water to the mixture to create bis-isoxazole diol; and nitrating the bis-isoxazole diol to create 3,3'-bis-isoxazole-5,5'-bis-methylene dinitrate, wherein the 3,3'-bis-isoxazole-5,5'-bis-methylene dinitrate comprises the structural formula:

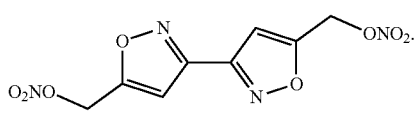

The alcohol containing an alkyne functional group may comprise propargyl alcohol. The salt compound may comprise sodium bicarbonate. The method may further comprise nitrating the bis-isoxazole diol with nitric acid. The nitric acid may comprise at least a concentration of 90% nitric acid in water. Alternatively, the method may further comprise nitrating the bis-isoxazole diol with 100% nitric acid and acetic anhydride. The salt compound and the water may be added to the mixture over at least a six-hour period. The method may further comprise mixing the mixture after adding the salt compound and the water for at least ten hours. The mixing of the dichloroglyoxime with an alcohol containing an alkyne functional group in methanol may occur at a concentration of 0.1M.

Another embodiment provides a compound having the structural formula:

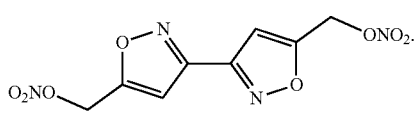

The compound may be formed by mixing dichloroglyoxime with an alcohol containing an alkyne functional group in methanol to create a mixture; adding a salt compound and water to the mixture to create bis-isoxazole diol; and nitrating the bis-isoxazole diol to create 3,3'-bis-isoxazole-5,5'-bis-methylene dinitrate. The alcohol containing an alkyne functional group may comprise propargyl alcohol. The salt compound may comprise sodium bicarbonate. The nitration may occur with nitric acid. The nitric acid may comprise at least a concentration of 90% nitric acid in water. Alternatively, the nitration may occur with 100% nitric acid and acetic anhydride. The salt compound and the water may be added to the mixture over at least a six-hour period. The mixture may be mixed after adding the salt compound and the water for at least ten hours. The mixing of the dichloroglyoxime with an alcohol containing an alkyne functional group in methanol may occur at a concentration of 0.1M.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which.

DETAILED DESCRIPTION

Figure 1:
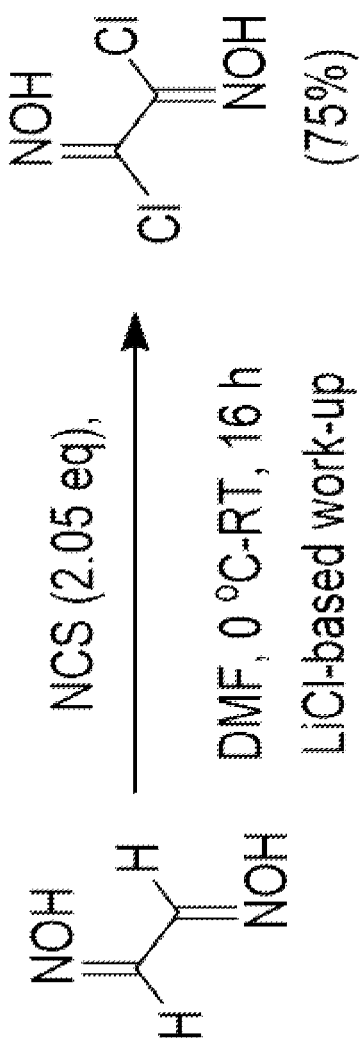
FIG. 1 illustrates a chemical diagram of the synthesis of dichloroglyoxime according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

In an effort to mitigate the aforementioned safety concerns, there is interest to synthesize materials that: a) possess a heterocyclic base having non-bonded electron lone pairs available for Lewis base behavior towards electrophilic energetic materials such as nitrocellulose (NC) and nitramines; b) possess alkyl nitrate pendant chains to ensure high miscibility with commonly used energetic plasticizers. Such materials may be looked upon as potentially having better wetting and plasticization properties, thus creating softer boundaries at material interfaces, leading to more robust propellant formulations. This may result in less volatility/migration during thermal and mechanical shock, as well as leaving the plasticizer in nitrocellulose for longer periods of time during cook-off, thus reducing surface area at time of ignition.

The embodiments herein provide an efficient and scalable synthesis of 3,3'-bis-isoxazole-5,5'-bis-methylene dinitrate. The material has favorable sensitivity properties, energetic properties point toward its potential as both a melt-castable secondary explosive, and as a propellant plasticizer. Referring now to the drawings, and more particularly to FIGS. 1 through 11, where similar reference characters denote corresponding features consistently throughout the figures, there are shown preferred embodiments.

In synthesizing materials that possess both a heterocyclic base and alkyl nitrate groups, an isoxazole-based heterocyclic system is used. The isoxazole ring not only has a non-bonded electron lone pair, but the carbon atoms that make up its molecular structure also allows for the introduction of alkyl nitrate pendant chains to a greater extent than tetrazoles or triazoles would.

FIG. 1 illustrates a chemical synthesis for making isoxazole-based energetic material according to an embodiment herein. One method to produce isoxazoles is through the cycloaddition of hydroximoyl chloride with nitrile oxides in the presence of a base. An intermediate containing the hydroximoyl chloride moiety that is found in energetic syntheses is dichloroglyoxime, as shown in FIG. 1.

Figure 2:
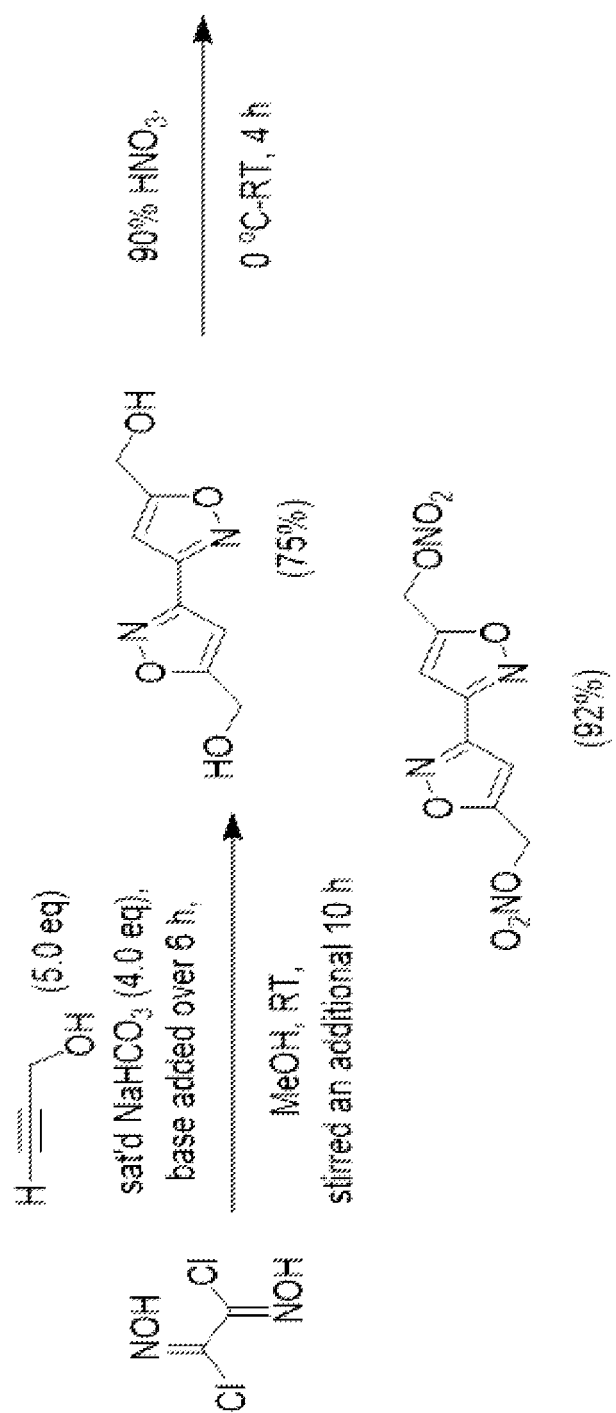
FIG. 2 illustrates a chemical diagram of the synthesis of bis-isoxazole diol and dinitrate according to an embodiment herein.
Figure 3:
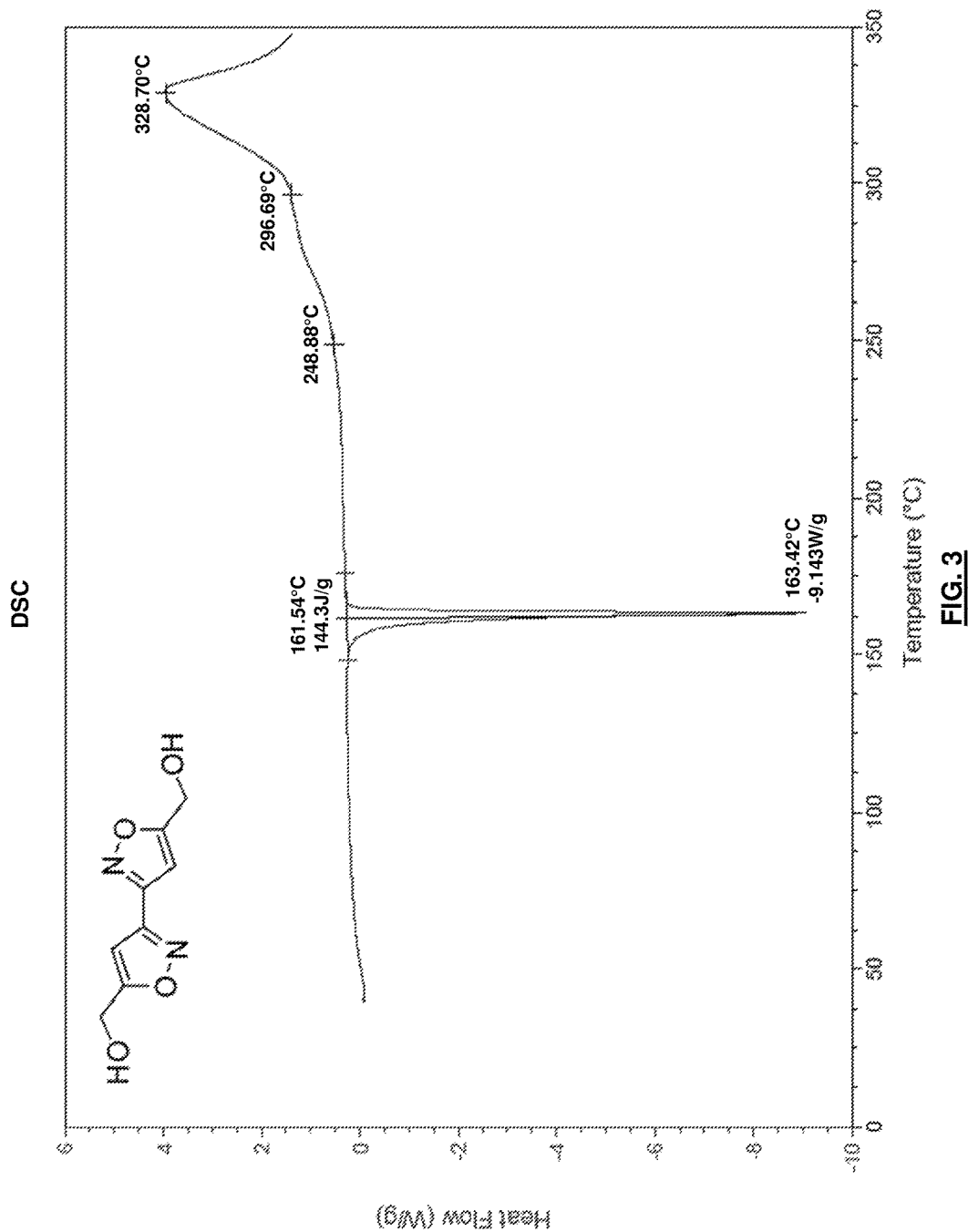
FIG. 3 is a graphical illustration of an infrared (IR) spectra of 5,5'-Dihydroxymethyl-3,3'-bis-isoxazole according to an embodiment herein.
Figure 4:
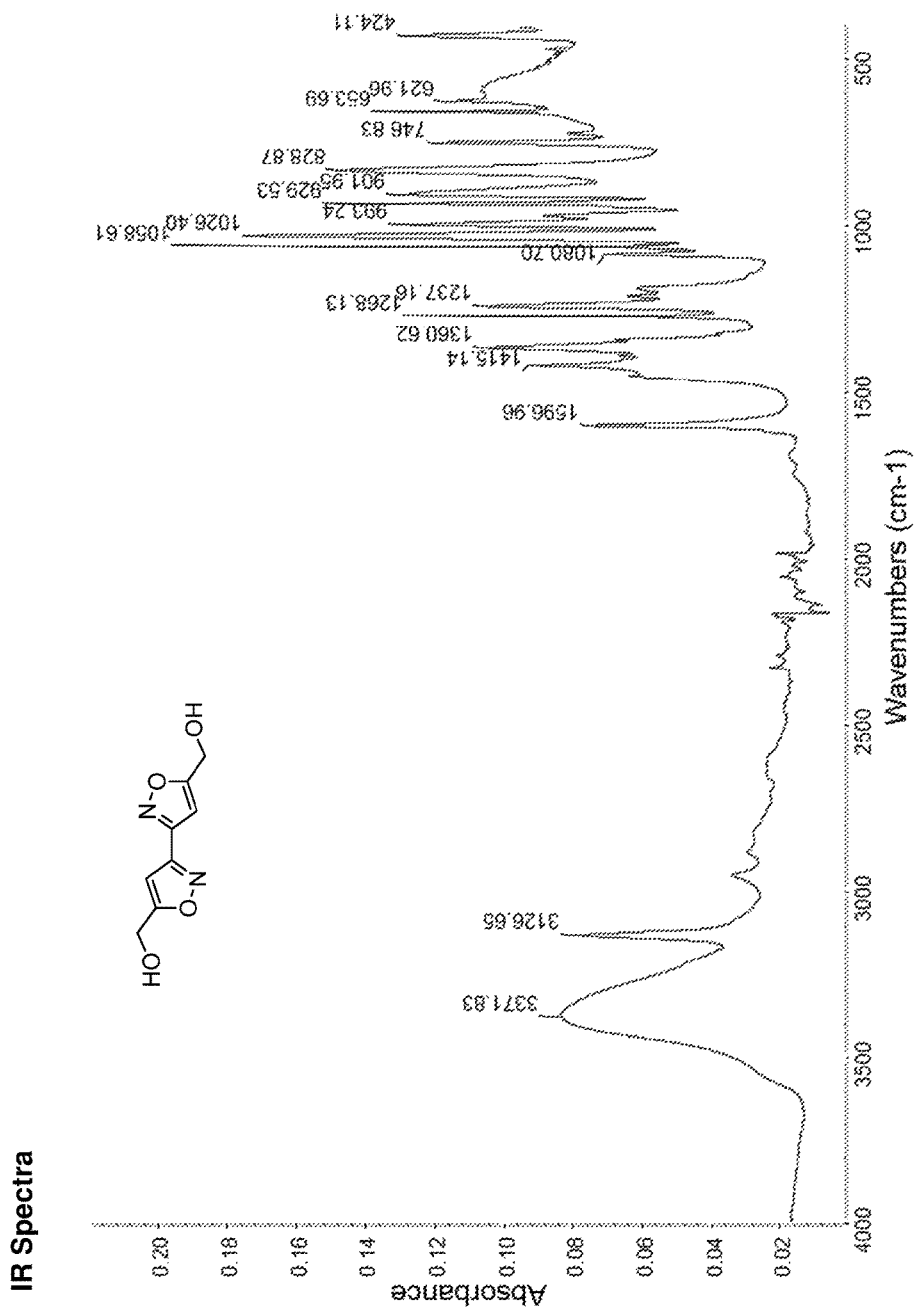
FIG. 4 is a graphical illustration of an $^1$H nuclear magnetic resonance (NMR) spectra of 5,5'-Dihydroxymethyl-3,3'-bis-isoxazole according to an embodiment herein.
Figure 5:
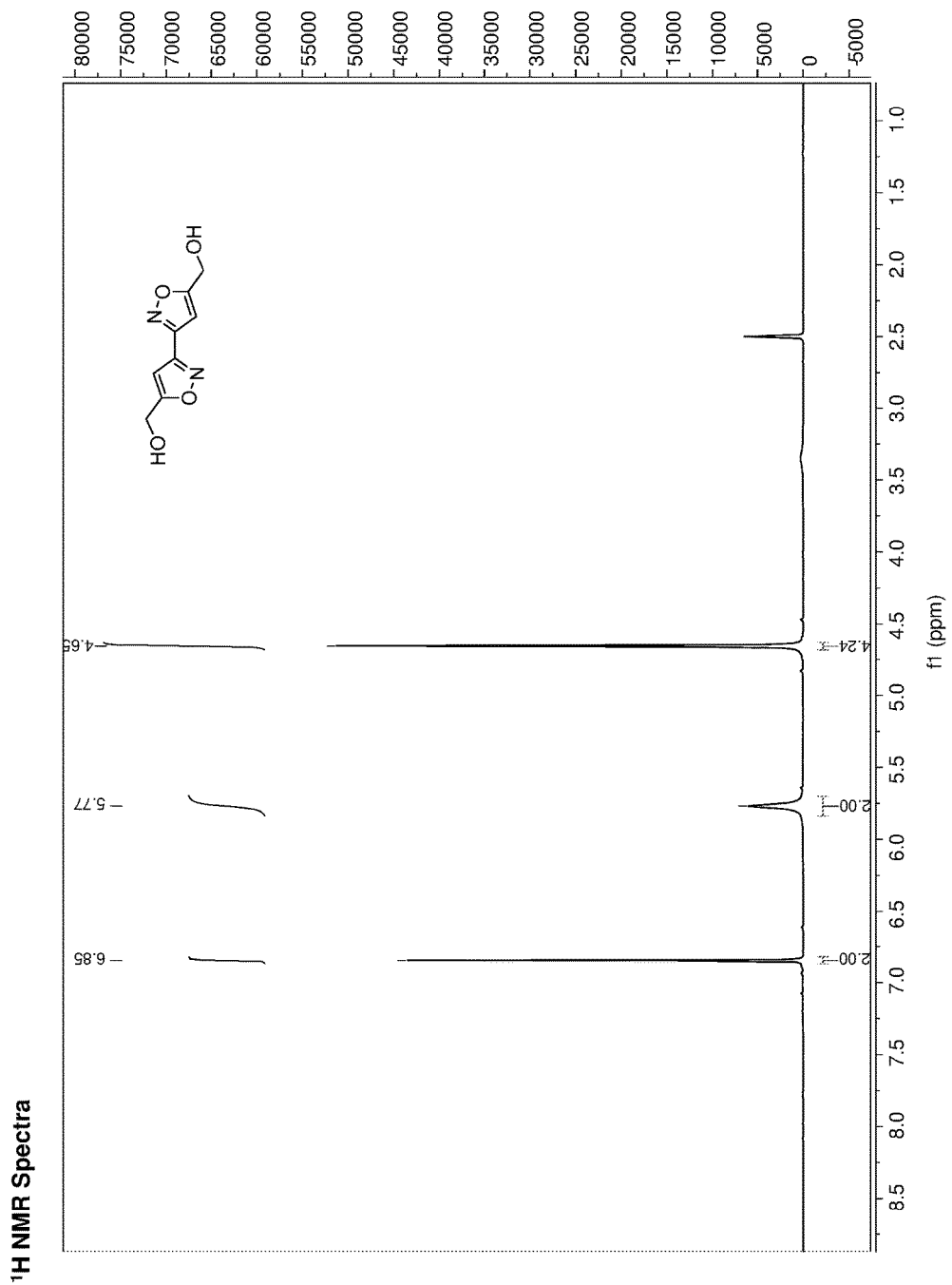
FIG. 5 is a graphical illustration of an $^{13}$C NMR spectra of 5,5'-Dihydroxymethyl-3,3'-bis-isoxazole according to an embodiment herein.
Figure 6:
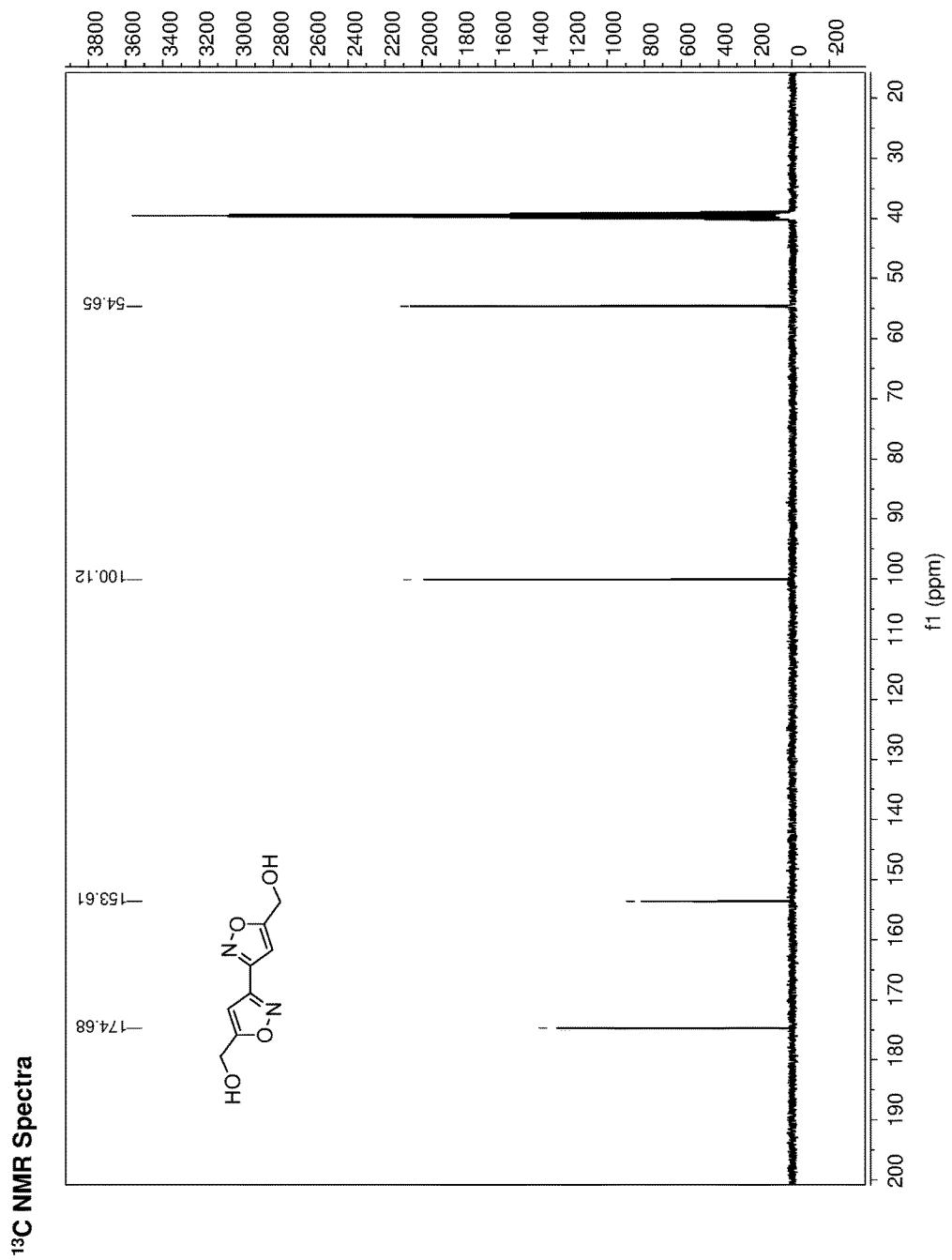
FIG. 6 is a graphical illustration of differential scanning calorimetry (DSC) curves of 5,5'-Dihydroxymethyl-3,3'-bis-isoxazole according to an embodiment herein.
Figure 7:
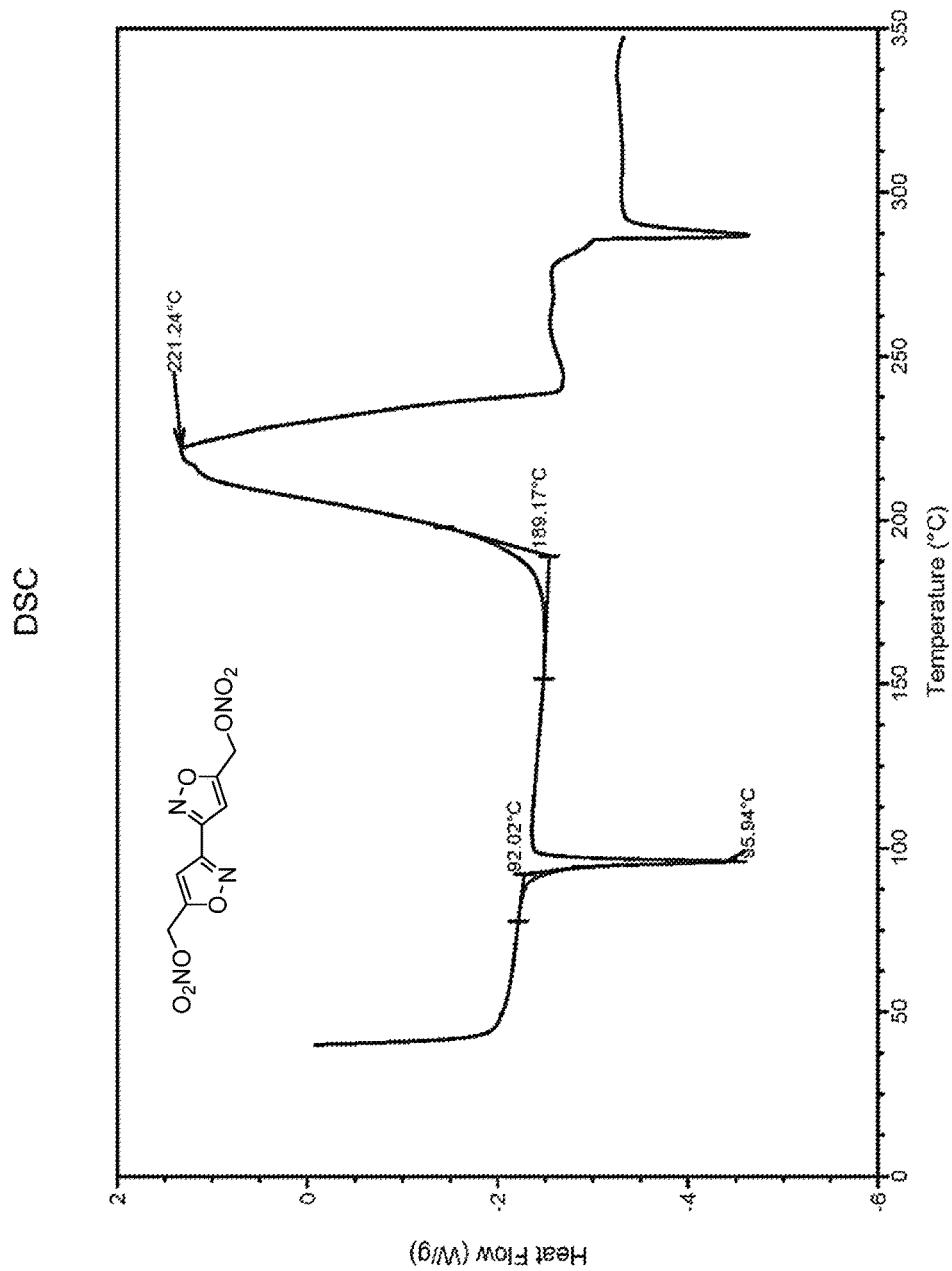
FIG. 7 is a graphical illustration of an IR spectra of 3,3'-bis-isoxazole-5,5'-bis-methylene dinitrate according to an embodiment herein.
Figure 8:
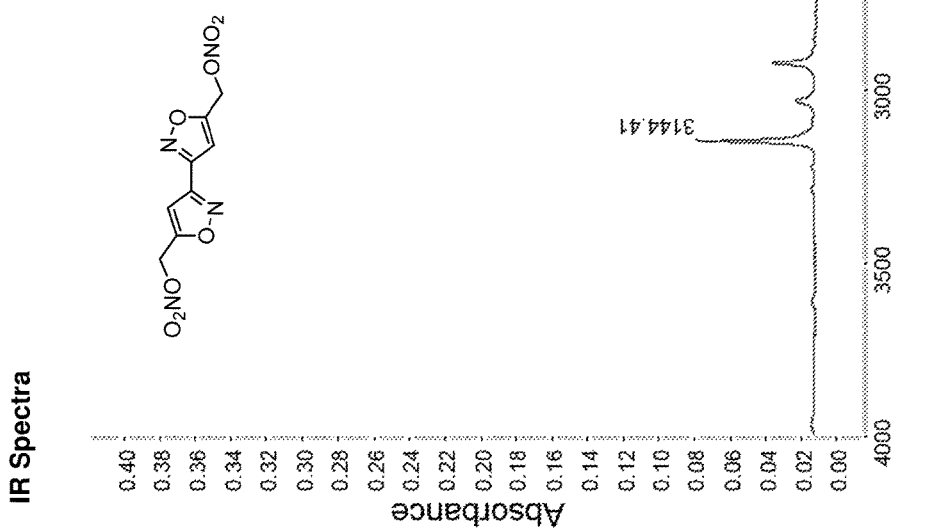
FIG. 8 is a graphical illustration of an $^1$H NMR spectra of 3,3'-bis-isoxazole-5,5'-bis-methylene dinitrate according to an embodiment herein.
Figure 9:
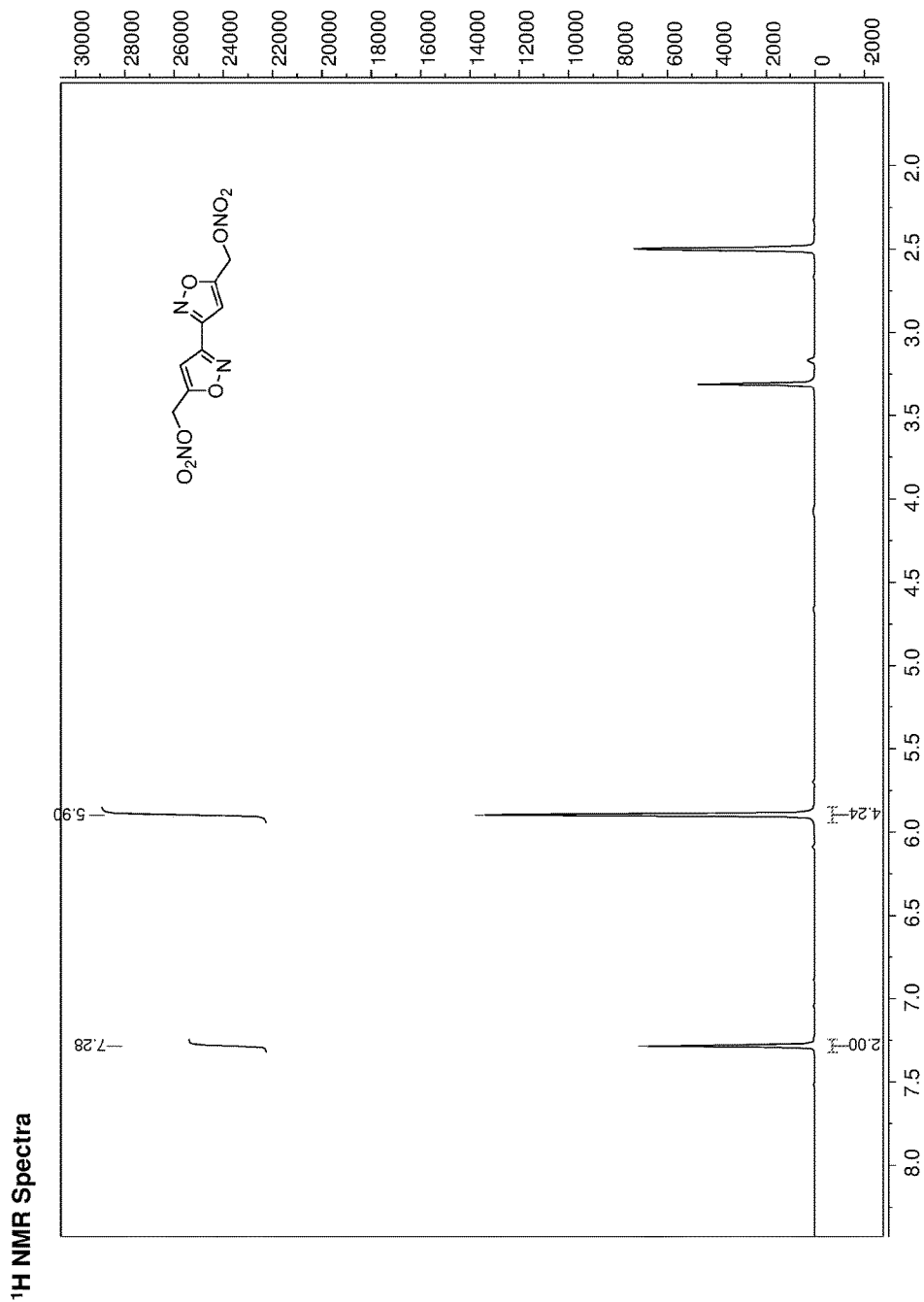
FIG. 9 is a graphical illustration of an $^{13}$C NMR spectra of 3,3'-bis-isoxazole-5,5'-bis-methylene dinitrate according to an embodiment herein.
Figure 10:
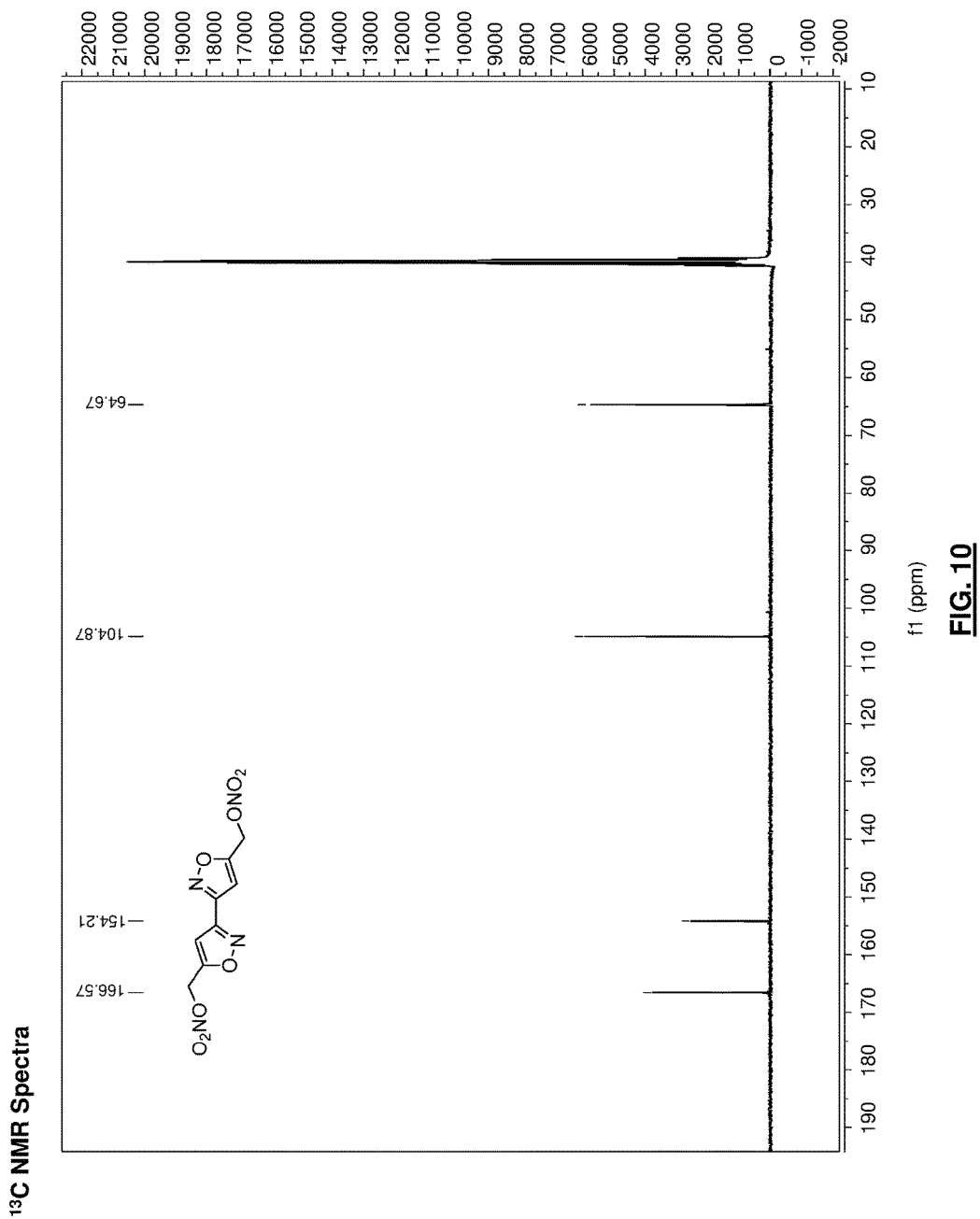
FIG. 10 is a graphical illustration of DSC curves of 3,3'-bis-isoxazole-5,5'-bis-methylene dinitrate according to an embodiment herein.

With dichloroglyoxime in hand, attention is turned to making the 3,3'-bis-isoxazole ring system. This ring system is likely formed by a stepwise process, wherein a mono-nitrile oxide is formed. This intermediate rapidly combines with the alkyne in situ before subsequent dechlorination to generate a second mono-nitrile oxide, which then undergoes a second cycloaddition to yield the product. It has been well established by the industry that undesired dimerization/oligomerization/polymerization events associated with nitrile oxides can be minimized if the reactions are performed while employing an excess of the alkyne. Bearing this in mind, the synthesis of bis-isoxazole diol is provided as shown in FIG. 2.

Dichloroglyoxime and an excess of propargyl alcohol is mixed in MeOH at 0.1M concentration. A saturated solution of $NaHCO_3$ is then added over a 15-minute period to convert dichloroglyoxime to the cycloadduct. The addition of a saturated solution of $NaHCO_3$ to the reaction mixture over a 6 hour period results in gentle bubbling, and a yellow solution, which is stirred for an additional 10 hours after addition. As a result, bis-isoxazole diol is obtained in 75% yield by simple evaporation of the solvent, followed by addition of water, and filtration of the resulting suspended solid. Use of a large excess of propargyl alcohol can be used to maximize the isolated yield in this instance.

Nitration of bis-isoxazole diol to produce 3,3'-bis-isoxazole-5,5'-bis-methylene dinitrate (BIDN) is high yielding. The bis-isoxazole diol is nitrated successfully when treated with a mixture of 100% $HNO_3/Ac_2O$, 100% $HNO_3$, and even with 90% $HNO_3$. Merely treating the bis-isoxazole diol with 70% $HNO_3$ does not result in the formation of dinitrate, and only starting material is recovered.

With BIDN synthesized, the sensitivity and performance profile on the material can be determined. The impact, friction, and ESD sensitivities of this material are summarized in Table 1. Compared to a class 1 sample of RDX, BIDN is less sensitive across-the-board, having reduced sensitivities to impact, friction, and electrostatic discharge. In Table 1, a higher value means that a greater amount of energy is needed to detonate or initiate the material. Therefore, the higher number values associated with BIDN indicates that BIDN is a less sensitive material compared to RDX.

TABLE 1

Sensitivities of 3,3'-bis-isoxazole-5,5'-bis-methylene dinitrate

| Compound | IS[a] [J] | FS[b] [N] | ESD[c] [J] |
|---|---|---|---|
| RDX | 6.2 | 141 | 0.125 |
| BIDN | 11.2 | >360 | 0.250 |

[a]IS = impact sensitivity, $h_{50}$ value
[b]FS = friction sensitivity
[c]ESD = electrostatic discharge The performance properties of BIDN are summarized in Table 2. This compound exhibits a fairly rare feature of nitrate ester energetic materials in that its melting point (92.0° C.) begins significantly below its temperature of decomposition (189.2° C.). Given the temperature profile and low sensitivity of dinitrate, coupled with its calculated detonation pressure and detonation velocity, this material could potentially be a TNT replacement in melt-castable formulations. This includes Composition B- and DNAN-based formulations. In addition, BIDN has a calculated specific impulse (Isp) of 206.2 s, possesses some Lewis basic character, and pendant alkyl nitrate functionality. Hence, this material may serve as an energetic plasticizer in insensitive munitions and in nitrate-based propellant formulations, and could reduce volatility/migration during thermal and mechanical shock.

TABLE 2

Properties of 3,3'-bis-isoxazole-5,5'-bis-methylene dinitrate

| Data category | BIDN | TNT | NG |
|---|---|---|---|
| $T_m$ [° C.][a] | 92.0 | 80.4 | 14 |
| $T_{dec}$ [° C.][b] | 189.2 | 295.0 | 50.0 |
| $\Omega_{CO2}$ [%][c] | −61.5 | −74 | 3.5 |
| $\Omega_{CO}$ [%][d] | −16.8 | −24.7 | 24.7 |
| $\rho$ [gcm$^{-3}$][e] | 1.585 | 1.654 | 1.6 |
| $P_{cj}$ [GPa][f] | 19.3 | 20.51 | 25.3 |
| $V_{det}$ [ms$^{-1}$][g] | 7060 | 6950 | 7700 |
| $I_{sp}$ [s][h] | 206.2 | — | 243.8 |
| $\Delta_f H°$ [kJmol$^{-1}$][i] | −139 | −59.3 | −370 |

[a]$T_m$ = onset temperature of melting
[b]$T_{dec}$ = onset temperature of decomposition
[c]$\Omega_{CO2}$ = $CO_2$ oxygen balance
[d]$\Omega_{CO}$ = CO oxygen balance
[e]$\rho$ = experimental density
[f]$P_{cj}$ = detonation pressure
[g]$V_{det}$ = detonation velocity
[h]$I_{sp}$ = specific impulse
[i]$\Delta_f H°$ = molar enthalpy of formation The embodiments herein provide an efficient scalable synthesis for generating dinitrate, which exhibits a low sensitivity to impact, friction, and electrostatic discharge. The sensitivity profile and performance properties of dinitrate suggest that this material may serve as: a) A TNT replacement in melt-castable formulations. This includes Composition B- and DNAN-based formulations; and b) an energetic plasticizing ingredient with nitrocellulose-based propellant formulations in an effort to reduce the volatility/migration issues that arise during cook-off.

EXPERIMENTAL EXAMPLES

Chemicals and solvents are used as received from commercial providers. $^1$H spectra can be recorded using a 400 MHz Bruker instrument, for example. $^{13}$C spectra can be recorded using a 100 MHz Bruker instrument, for example. The chemical shifts refer to typical standard tetramethylsilane (H, C) in DMSO-$d_6$ as the solvent. Melting points and decomposition temperatures can be measured at a heating rate of 5° C./min using a TA instruments Q10 DSC instrument, for example. Infrared spectra can be measured with a Bruker Alpha-P FTIR instrument, for example.

Impact sensitivity testing may be performed using a modified drophammer, for example, and friction sensitivity may be performed using a BAM friction apparatus in accordance with NATO STANAG guidelines, for example. ESD sensitivity testing can be performed using an ABL testing machine, for example.

Example Synthesis of 5,5'-Dihydroxymethyl-3,3'-bis-isoxazole

To a 5 L round-bottom flask equipped with a stirbar add 1.9 L of MeOH, dichloroglyoxime (30 g, 0.191 mol, 1.00 eq), and propargyl alcohol (53.6 g, 55.2 mL, 0.956 mol, 5.00 eq). To the reaction mixture add a 30 wt % solution of $NaHCO_3$ (64.3 g, 670 mL, 0.77 mol, 4.00 eq) over 6 hours. After addition of the base is completed, the reaction mixture is stirred for an additional 10 hours. The reaction mixture is transferred to a rotary evaporator, and is concentrated in vacuo. To the resultant solid material add 2 L of $H_2O$, and the reaction mixture is cooled to 0° C. The solid is collected by Büchner filtration, transferred to a drying tray, and dried for 16 hours in a well-ventilated fume hood to afford 28.1 g (75%) of bis-isoxazole as an off-white powder: m.p.=163.4° C. (peak) (shown in FIG. 3); IR: $v_{OH}$=3371 cm$^{-1}$ (shown in FIG. 4), NMR: $^1$H (400 MHz, DMSO-$d_6$), 6.85 (s, 2H, —CH), 5.77 (broad s, 2H, —OH), 4.65 (s, 4H, —CH$_2$—OH) (shown in FIG. 5). $^{13}$C NMR (100 MHz, DMSO-$d_6$), 174.68 (N—C—C), 153.61 (O—C—C), 100.12 (—CH), 54.65 (—CH$_2$—) (shown in FIG. 6).

Example Synthesis of 3,3'-bis-isoxazole-5,5'-bis-methylene dinitrate

To a 250 mL round-bottom flask equipped with a stirbar add 150 mL of 90% HNO$_3$. The flask is cooled to 0° C. in an ice-water bath, and bis-isoxazole (17.6 g, 0.120 mol, 1.00 eq) is added portionwise over a 10 min period. No exothermic reaction is observed during addition. The reaction mixture is left in the ice-water bath and stirred for 4 hours, during which time the ice-water bath melts, and the reaction mixture warms to room temperature. The reaction mixture is poured onto ice, a white solid forms, and this solid is collected by Büchner filtration. The solid is left to dry on the Buchner funnel under suction for 3 hours in a well-ventilated fume hood to afford 23.6 g (92%) of dinitrate as a white powder: m.p.=92.0° C. (onset), 95.9° C. (peak); $T_{dec}$=189.2° C. (onset), 221.2° C. (peak) (shown in FIG. 7); IR: $v_{NO}$=1643, 1605 cm$^{-1}$ (shown in FIG. 8); NMR: $^1$H (400 MHz, DMSO-d$_6$), 7.28 (s, 2H, —CH), 5.90 (s, 4H, —CH$_2$—ONO$_2$) (shown in FIG. 9); $^{13}$C NMR (100 MHz, DMSO-d$_6$), 166.57 (N—C—C), 154.21 (O—C—C), 104.87 (—CH), 64.67 (—CH$_2$—) (shown in FIG. 10)

Figure 11:
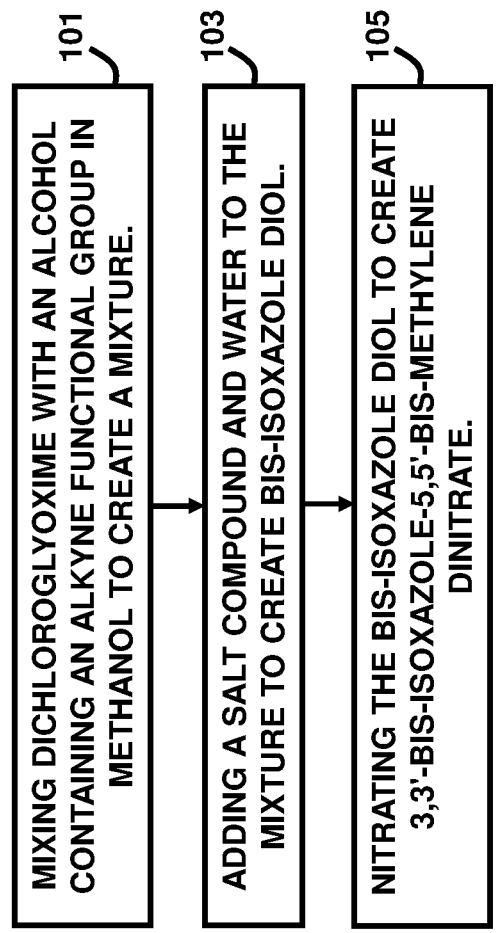
FIG. 11 is a flow diagram illustrating a method according to an embodiment herein.

FIG. 11, with reference to FIGS. 1 through 10, is a flow diagram illustrating a method according to an embodiment herein. The method comprises mixing (101) dichloroglyoxime with an alcohol containing an alkyne functional group in methanol to create a mixture; adding (103) a salt compound and water to the mixture to create bis-isoxazole diol; and nitrating (105) the bis-isoxazole diol to create 3,3'-bis-isoxazole-5,5'-bis-methylene dinitrate, wherein the 3,3'-bis-isoxazole-5,5'-bis-methylene dinitrate comprises the structural formula:

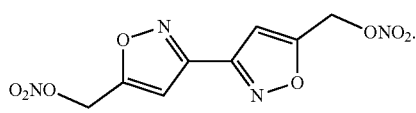

The alcohol containing an alkyne functional group may comprise propargyl alcohol. The salt compound may comprise sodium bicarbonate. The method may further comprise nitrating the bis-isoxazole diol with nitric acid. The nitric acid may comprise at least a concentration of 90% nitric acid in water. Alternatively, the method may further comprise nitrating the bis-isoxazole diol with 100% nitric acid and acetic anhydride. The salt compound and the water may be added to the mixture over at least a six-hour period. The method may further comprise mixing the mixture after adding the salt compound and the water for at least ten hours. The mixing of the dichloroglyoxime with an alcohol containing an alkyne functional group in methanol may occur at a concentration of 0.1M.

BIDN has several potential military applications including use as: (1) An ingredient in melt-castable explosive formulations. This includes a replacement for TNT-based formulations. This includes Composition B-, and DNAN-based formulations. (2) An energetic plasticizer to replace and/or supplement diethylene glycol dinitrate (DEGDN) and triethylene glycol dinitrate (TEGDN) in double-base propellant formulations. (3) An energetic plasticizer to replace and/or supplement the non-energetic phthalate-based, adipate-based, and triacetin-based propellant plasticizer ingredients in rocket and gun propellant applications. (4) A plasticizing ingredient that assists in making up the general formulation of double-based propellants.

BIDN also has several potential commercial applications including enhanced handling, processing and detooling during the use of BIDN as an insensitive, yet energetic ingredient in typical mixing, casting and curing of modern, castable minimum signature rocket propellants. BIDN may offer enhanced energy and enhanced processing safety and handling to the overall propellant making for a more competitive, less sensitive version of said propellant since it may plasticize nitrocellulose more effectively. Similarly, BIDN may not take large mass quantities with specific formulations to make major improvements to processing safety, handling, tooling and machining of such propellants. BIDN may offer tremendous plasticization of higher nitrogen nitrocellulose stocks (typically >12.6% N content), allowing for the use of higher nitrogen content nitrocellulose with higher resultant mechanical properties. Typical energetic plasticizers used in minimum signature propellants either as extruded or castable, notably nitroglycerin (NG) and 1, 2, 4-butanetriol-trinitrate (BTTN) suffer from high mechanically sensitivity (impact, friction) and/or thermal stability issues since they contain secondary nitrate ester functionalities. Since BIDN contains only primary nitrate functionalities, it may offer reduced cost in aging, surveillance, and demilitarization costs with longer propellant shelf lives with reduced aging issues often typical of double base propellant based on energetic nitrate ester plasticizers which contain secondary nitrate ester functionalities. Finally, higher thermally stable propellants using BIDN as an energetic plasticizer would exhibit lower vapor pressure and slower aging. This may assist typical tactical platforms exposed to large thermal extremes or extended periods of thermal stress with lowered migration rates within and out/into propellants to the external environment and/or liner.

Another element that hinders most commonly fielded double base minimum signature castable propellants is poor responses to bullet/fragment insults, slow cook-off scenarios, and shape charge jet threats. Much of this is due to the high volatility and reactivity of the entrained nitrate ester plasticizer notably nitroglycerine when subjected to such scenarios. BIDN can achieve significant improvements to this type of application, with its higher molecular interactions within the plasticizer matrix of said formulations, resulting in more homogenous, less sensitive propellants.

Other potential uses of BIDN include pressed and/or extruded dynamite formulations where heat of explosion is often controlled only by alteration of nitroglycerine content. The use of an insensitive, yet energetic plasticizer with reduced volatility enhances the manufacture, transportation, and storage of said novel dynamites. Likewise, higher thermal stability with lower vapor pressure and slower aging may assist in high thermal performance areas such as those in underground mining and deep petroleum fracking.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A method comprising:
   mixing dichloroglyoxime with an alcohol containing an alkyne functional group in methanol to create a mixture;
   adding a salt compound and water to said mixture to create bis-isoxazole diol; and
   nitrating said bis-isoxazole diol to create 3,3'-bis-isoxazole-5,5'-bis-methylene dinitrate.

2. The method of claim 1, wherein said 3,3'-bis-isoxazole-5,5'-bis-methylene dinitrate has the structural formula:

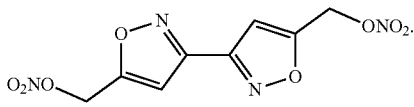

3. The method of claim 1, wherein said alcohol containing an alkyne functional group is propargyl alcohol.

4. The method of claim 1, wherein said salt compound is comprises sodium bicarbonate.

5. The method of claim 1, wherein said nitrating comprises nitrating said bis-isoxazole diol with nitric acid.

6. The method of claim 5, wherein said nitric acid comprises at least a concentration of 90% nitric acid in water.

7. The method of claim 1, wherein said nitrating comprises nitrating said bis-isoxazole diol with 100% nitric acid and acetic anhydride.

8. The method of claim 1, wherein said salt compound and said water are added to said mixture over at least a six-hour period.

9. The method of claim 8, further comprising mixing said mixture after adding said salt compound and said water for at least ten hours.

10. The method of claim 1, wherein said mixing results in 0.1M dichloroglyoxime in methanol.

11. A compound having the structural formula:

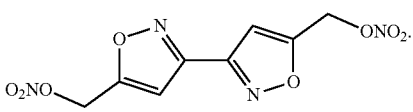

12. A 3,3'-bis-isoxazole-5,5'-bis-methylene dinitrate compound formed by:
   mixing dichloroglyoxime with an alcohol containing an alkyne functional group in methanol to create a mixture;
   adding a salt compound and water to said mixture to create bis-isoxazole diol; and
   nitrating said bis-isoxazole diol to create 3,3'-bis-isoxazole-5,5'-bis-methylene dinitrate.

13. The compound of claim 12, wherein said alcohol containing an alkyne functional group is propargyl alcohol.

14. The compound of claim 12, wherein said salt compound is sodium bicarbonate.

15. The compound of claim 12, wherein the nitration occurs with nitric acid.

16. The compound of claim 15, wherein said nitric acid comprises at least a concentration of 90% nitric acid in water.

17. The compound of claim 12, wherein the nitration occurs with 100% nitric acid and acetic anhydride.

18. The compound of claim 12, wherein said salt compound and said water are added to said mixture over at least a six-hour period.

19. The compound of claim 12, wherein said mixture is mixed after adding said salt compound and said water for at least ten hours.

20. The compound of claim 12, wherein said mixing results in 0.1M dichloroglyoxime in methanol.

* * * * *